(12) United States Patent  
Härer et al.

(10) Patent No.: US 8,150,131 B2  
(45) Date of Patent: Apr. 3, 2012

(54) COMPUTER TOMOGRAPHY METHOD FOR DETERMINING AN OBJECT REGION WITH THE AID OF PROJECTION IMAGES

(75) Inventors: Wolfgang Härer, Erlangen (DE); Ernst-Peter Rührnschopf, Erlangen (DE); Bernhard Scholz, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 680 days.

(21) Appl. No.: 12/317,061

(22) Filed: Dec. 18, 2008

(65) Prior Publication Data

US 2009/0175407 A1 Jul. 9, 2009

(30) Foreign Application Priority Data

Jan. 4, 2008 (DE) .................. 10 2008 003 173

(51) Int. Cl.
*G06K 9/00* (2006.01)
*G06K 9/48* (2006.01)
*H01L 27/00* (2006.01)
(52) U.S. Cl. .............. 382/131; 382/199; 250/208.1
(58) Field of Classification Search ............ 382/128, 382/130–132, 190, 199, 203, 286, 288, 291; 378/4–27; 250/208.1
See application file for complete search history.

(56) References Cited

U.S. PATENT DOCUMENTS

| 6,339,223 | B1 * | 1/2002 | Motomura et al. ...... 250/363.07 |
| 7,515,677 | B2 * | 4/2009 | Zellerhoff .................... 378/4 |
| 7,916,829 | B2 * | 3/2011 | Harer et al. ................... 378/7 |
| 2002/0126884 | A1 * | 9/2002 | Gerritsen et al. ............ 382/131 |
| 2005/0169526 | A1 * | 8/2005 | Romsdahl et al. .......... 382/173 |
| 2007/0093711 | A1 * | 4/2007 | Hoheisel et al. ............ 600/407 |
| 2007/0230652 | A1 * | 10/2007 | Scholz et al. .................. 378/4 |
| 2008/0089468 | A1 * | 4/2008 | Heigl et al. ................... 378/20 |

FOREIGN PATENT DOCUMENTS

| DE | 10 2005 022 540 A1 | 11/2006 |
| DE | 10 2006 062 277 A1 | 6/2008 |
| EP | 0 106 964 A2 | 5/1984 |

OTHER PUBLICATIONS

Zellerhoff et al.; "Low contrast 3D reconstruction from C-arm data"; Proceedings of SPIE, Medical Imaging 2005; pp. 646-655; vol. 5745.
Fieldcamp et al.; "Practical Cone-beam Algorithm"; Journal of the Optical Society of America; Jun. 1984; pp. 612-619; vol. 1, No. 6. A1.
Savitzky et al.; Smoothing and differentiation of data by simplified least squares procedures:; Analytical Chemistry; Jul. 1964; pp. 1627-1639; vol. 36; No. 8.
Hsieh et al..; "An iterative approach to the beam hardening correction in cone beam CT"; Med. Phys.; Jan. 2000; pp. 23-29; vol. 27, 20 1.

(Continued)

*Primary Examiner* — Que T Le
*Assistant Examiner* — Pascal M Bui Pho (57) ABSTRACT

In a computer tomography method an object region of the object being examined is determined in that projection beams that are linked with maximum attenuation are sought in cropped projection images. A central point of the object region is then determined and the object sections associated with the projection beams plotted on the central point. The object region can be at least approximately determined using the end points of the object sections.

19 Claims, 3 Drawing Sheets

OTHER PUBLICATIONS

Kyriakou et al.; "Combining deterministic and Monte Carlo calculations for fast estimation of scatter intensities in CT"; Phys. Med. Biol. 51; 2006; pp. 4567-4586; ICMP 2005.; IOP Publishing Ltd.

Bensen et al.; "Framework for Iterative Cone-Beam Micro-CT Reconstruction"; IEEE Transactions on Nuclear Science; Oct. 5, 2005; pp. 1335-1340; vol. 52, No. 5.

Sourbelle et al, "Reconstruction from Truncated Projections in CT Using Adaptive Detruncation", Journal European Radiology, May 2005, pp. 1008-1014, vol. 15, No. 5.

Hsieh et al., "A Novel Reconstruction Algorithm to Extend the CT Scan Field o-of-View", Medical Physics, Sep. 2004, pp. 2385-2391, vol. 31, No. 9.

Wiesent et al.; "Enhanced 3-D-Reconstruction Algorithm for C-Arm Systems Suitable for Interventional Procedures"; IEEE Trans. Med. Imaging, vol. 19, No. 5, May 2000, pp. 391-403.

Press et al.; "Numerical Recipes in C. The art of scientific computing" Second Edition, Kapitel 14.8 Savitzky-Golay Smoothing Filters.; 1992; pp. 650-655; 0-521-43108-5.

* cited by examiner

COMPUTER TOMOGRAPHY METHOD FOR DETERMINING AN OBJECT REGION WITH THE AID OF PROJECTION IMAGES

CROSS REFERENCE TO RELATED APPLICATIONS

This application claims the benefits of German application No. 10 2008 003 173.9 filed Jan. 4, 2008 and is incorporated by reference herein in its entirety.

FIELD OF INVENTION

The invention relates to a computer tomography method for determining a region taken up by an object being examined with the aid of projection images, comprising the method steps:
generating radiation using a radiation source;
X-raying the object from various directions of projection;
loading a detector with the radiation and detecting via the detector the projection images of the object associated with the various directions of projection; and
creating object images by way of an evaluation unit connected downstream of the detector.

BACKGROUND OF THE INVENTION

A method of this kind is known from SOURBELL, K.; KACHELRIESS, M.; KALENDER, W. A.: Reconstruction from truncated projections in CT using adaptive detruncation, Journal European Radiology, vol. 15, no. 5, May 2005, pages 1008-1014. The known method is particularly suitable for use in CT scanners with flat panel detectors (FPD). Laminar multi-line detectors of this kind are used in connection with C-arm computer tomography but also with CT scanners with a fixed gantry. However, the flat panel detectors are often not large enough to completely capture the lateral extension of the patient volume penetrated by radiation. Cropped projection images, which are also called truncated projection images, often occur therefore. In the reconstruction of object images, which is carried out by the evaluation unit, use of truncated projection images leads to pronounced artifacts and large density errors in the reconstructed object images. The truncated projection images are frequently extrapolated to suppress the errors in the object images caused by truncation. To carry out the extrapolation it is advantageous if the object region taken up by the object being examined is at least approximately known before carrying out the extrapolation. In the known method parameters of an elliptical envelope are determined by taking account of pre-defined consistency conditions of a large number of projection images for determining the object region. The optimization that is to be performed in the known method can require a plurality of iterations and therefore needs a relatively large amount of computing.

An extrapolation method is known from HSIEH, J.; CHAO, E.; THIBAULT, J.; GREKOWICZ, B.; HORST, A.; MCOLASH, S.; MYERS, T. J.: A novel reconstruction algorithm to extend the CT scan field-of-view, Med. Phys. 31 (9), September 2004, pages 2385-2391, in which, at the boundary of a truncated projection image, parameters of an equivalent water cylinder are determined and the truncated projection images are extrapolated using the equivalent water cylinder.

From ZELLERHOFF, M.; SCHOLZ, B.; RUHRN-SCHOPF, E.-P.; BRUNNER, T.: Low contrast 3D reconstruction from C-arm data, Proceedings of SPIE, Medical Imaging 2005, vol. 5745, pages 646-655 a method for low-contrast representation in the three-dimensional reconstruction of tissue density distribution by means of C-arm computer tomography is also known. In this method a hybrid extrapolation is carried out in which, depending on the quality of the projection images at the cropped boundary, an extrapolation is performed with the aid of an equivalent water cylinder or by means of a Gaussian function. A method for beam hardening correction is also described in this document.

The cropped projection images can in principle also be processed using standard reconstruction algorithms. Standard reconstruction algorithms of the filtered back projection type are described for example in the publication FELDKAMP, L. A.; DAVIS, L. C.; KRESS, J. W.: Practical cone-beam algorithm, J. Opt. Soc. Amer. A, vol. 6, 1984, pages 612-619 and in the publication WIESENT, K.; BARTH, K.; NAVAB, N. et al.: Enhanced 3-D-Reconstruction Algorithm for C-Arm Systems Suitable for Interventional Procedures, IEEE Trans. Med. Imaging, vol. 19, no. 5, Mai 2000, pages 391-403.

Applying these standard reconstruction algorithms to truncated projection images leads to pronounced artifacts and large density errors in the reconstructed images, even if the cropped object regions lie outside of the reconstructed, examined region (ROI=region of interest). The correction algorithms mentioned in the introduction are therefore applied, with which the truncated data is extrapolated in the outer region where measuring data is missing.

SUMMARY OF INVENTION

Starting from this prior art the object underlying the invention is therefore to further improve correction of truncated projection images.

This object is achieved by a method with the features of the claims. Advantageous embodiments and developments are disclosed in the claims.

In the method the position of a central region of the object being examined is determined using at least two projection images taken from different directions of projection. Object sections, which characterize the extension of the object region and which are plotted on the central region transversely to the associated projection images, are then determined from projection values of the projection images. The end points of the object section can then be used for determining the extension of the object region. 'Central region' is in this case taken to mean in particular the region located inside the object, over which the cloud of points of intersection, focal points or connecting sections, which are determined according to one of the methods described in more detail below, extend(s). If a single central point is determined the central region can be the same as the central point.

This method provides the advantage that it can be carried out without great computing effort. In particular it may also be used if all projection images taken are truncated.

In a preferred embodiment the determined object section is symmetrically plotted on the central region. As it may be assumed that, as a rule, the object being examined has an at least approximately elliptical cross-section, symmetrical plotting of the object section leads to end points that lie approximately on the actual envelope of the object being examined.

In particular the central region can be determined in that the projection beam with maximum attenuation of the radiation through the object being examined is sought in at least two projection images. With homogenous objects the projection beam with maximum attenuation is the projection beam which runs through the center of the object being examined. Even with inhomogeneous objects it may be assumed that the radiation is maximally attenuated in the region of the center. A proximity region of the projection beams can then be determined. In this connection 'proximity region' is taken to mean the region of the object image space in which the projection beams come closest. In the case of intersecting projection beams this can be the point of intersection. Otherwise it should be taken to mean a connecting section which is perpendicular to both projection lines.

A central region, at which the determined object sections can be plotted, can accordingly be determined based on the points of intersection or connecting sections of all projection beams that have been determined using projection images taken from different directions of projection. The cloud of points of intersection can be regarded as the central region of the object being examined in this case.

A central point can also be determined by way of example by determining a large number of points of intersection of the projection beams and fixing the central point inside the cloud formed by the points of intersection.

The central point is preferably determined by averaging the points of intersection of two intersecting projection beams respectively. The influence of inhomogeneities in the attenuation coefficients in the object being examined can be reduced in this way.

Averaging is also preferably carried out in a weighted manner, the weight of a point of intersection of two projection beams being all the smaller, the smaller the acute angle is between the projection beams.

The object sections can each be plotted on the central point in the direction of the associated projection beam. It is also possible to project the central point onto the respective projection beam, for example at a right angle to the projection beam, and to use the projected central point for plotting the object section. The latter possibility is more complicated than the former, but by way of compensation the object section is plotted along the associated object beam, so increased accuracy in determining the object region is to be expected.

An object focal point, which is created using non-truncated images, can also be taken into account when determining the central point. This makes use of the fact that, apart from the coordinates in the direction of projection, the coordinates of a focal point of a projection image are the same as the coordinates of the object focal point. All coordinates of an object focal point can be determined using two non-truncated images therefore. The object focal point can then enter the averaging of the points of intersection or be used without further modification to plot the determined object sections.

It is also possible to determine boundary points in non-truncated projection images and to determine the associated boundary beams. Points of intersection of these boundary beams determined using various projection images can then be used in addition to the end points of the object section to determine the object region. The accuracy in determining the object region can be further improved thereby.

The object sections can be determined from the projection values by assuming an attenuation coefficient typical for the object being examined. As the basic nature of the object being examined is known a suitable attenuation coefficient can be used at least in the case of homogenous objects.

In the case of inhomogeneous objects of which the attenuation coefficient varies greatly locally, a mean attenuation coefficient can be estimated by totaling projection image values of an object image plane and the total is divided by the area of the at least approximately determined object region which lies in the object image plane being considered.

The end points of the object sections can be joined to form a hull polygon which is used as the external contour of the object region being determined. Points of intersection of boundary beams of the object being examined can optionally also be used for determining the hull polygon.

As most of the objects being examined are approximately cylindrical, it is usually sufficient if the object region is sought in an object image plane which contains a focal point of the radiation source.

In a modified embodiment the object regions in additional object image planes are also determined by projecting the projection beams, which run through the central region of the object being examined, and the object sections onto the object image plane being examined. A large number of object image regions arranged side by side in the axial direction can be determined in this way.

To reduce the computing effort it is expedient to subject the projection images taken from various directions of projection to smoothing before determining the object image region, so the result of the method is not distorted as a result of noise.

In order, finally, to keep the computing effort optimally low when determining the object region the spatial resolution of the object image space can be coarsened and the spatial resolution of the projection images decreased. Solely a subset of projection images with increased angular increment of the projection angle can be used moreover for determining the object image region.

BRIEF DESCRIPTION OF THE DRAWINGS

Further advantages and properties of the invention emerge from the following description in which exemplary embodiments of the invention are described in detail with reference to the drawings, in which.

DETAILED DESCRIPTION OF INVENTION

Figure 1:
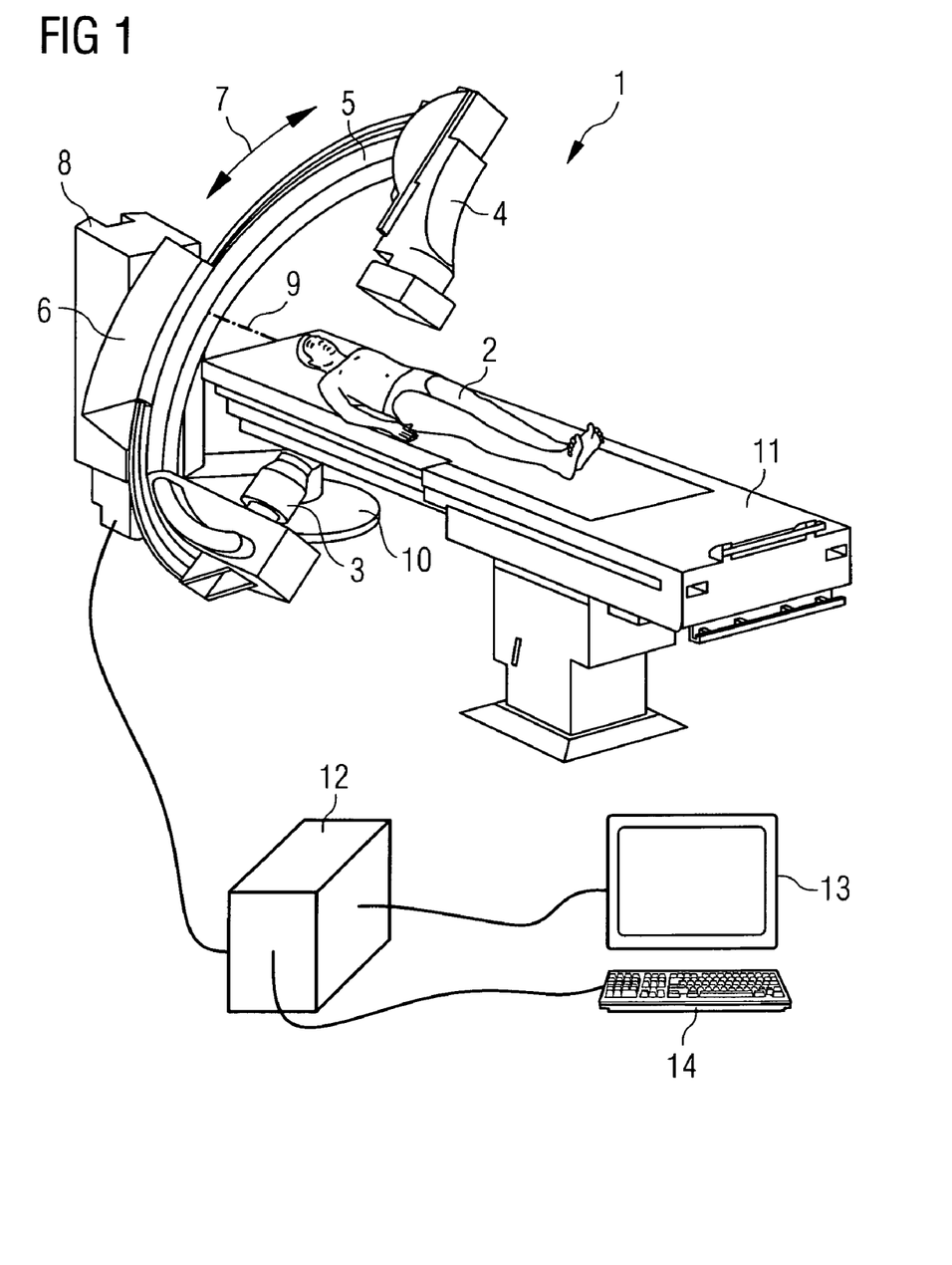
FIG. 1 shows a perspective view of an X-ray machine with a C-arm.

FIG. 1 shows a perspective view of an X-ray machine 1 which is suitable for X-ray imaging a patient 2. The body of the patient 2 constitutes the object being examined.

In detail the X-ray machine 1 comprises an X-ray tube 3 and a detector 4 which detects the X-ray radiation emitted by the X-ray tube 3. The detector 4 is preferably a digital flat panel detector. Nowadays flat panel detectors of this kind are produced with typical dimensions of about 20×20 cm² to 40×40 cm². These flat panel detectors comprise photodiodes made of amorphous silicon. There are no restrictions with respect to the size and materials used. By using a flat panel detector of this kind the X-ray machine 1 can be used in an intervention for both three-dimensional imaging and for two-dimensional X-raying. The X-ray machine is also suitable for angiography in which vessels are examined with the aid of contrast medium.

En route to the detector 4 the X-ray radiation passes through the patient 2, so the detector 4 takes projection images of the patient 2. As the X-ray radiation is partially attenuated in the body of the patient 2 by scattering or absorption, the projection images reproduce the attenuation of the X-ray radiation through the patient 2.

The X-ray tube 3 and the detector 4 are provided on the ends of a C-arm 5 which is held by an attachment 6. The C-arm 5 is mounted in the attachment 6 so as to be movable in a circumferential direction. The attachment 6 is in turn provided on a pedestal 8 so as to be swivelable about an axis of rotation 9. The pedestal 8 sits on a base 10 which allows the pedestal 8 to move on the floor.

During operation of the X-ray machine 1 the C-arm 5 typically executes a swiveling movement about the axis of rotation 9 and in the process revolves around a patient's couch 11 on which the patient 2 is supported. The C-arm 5 can also execute significantly more complex movements, which, in addition to a swiveling movement, include a movement in the circumferential direction 7 or a movement of the pedestal 8.

While the C-arm 5 is moving projection images are taken which below will also be called projections for short. The projection images are fed to an evaluation unit 12 which is connected downstream of the detector 4. The evaluation unit 12 creates object images of the parts of the body from the projection images that have been taken. These object images can be two-dimensional sectional views or three-dimensional volume images of the density distribution of the object being examined and can be displayed on a monitor 13 connected to the evaluation unit 12. Input devices 14 with which the X-ray machine 1 can be controlled are also connected to the evaluation unit 12. The monitor 13 can also be located directly above the patient's couch 11 while the input devices 14 are arranged in the region of the patient's couch 11, so the user can control the movement of the C-arm 5 and can monitor the internal structure of the body of the patient 2.

The method described in detail hereinafter constitutes a pre-processing step before the start of the actual reconstruction of the object images.

For the sake of simplicity two-dimensional fan beam geometry will be described first of all. The direct generalization to three-dimensional cone beam geometry is then easily possible.

It should also be noted that the method described in detail below can be used for X-ray equipment with a fixed gantry as well as for X-ray equipment of the type of X-ray machine 1.

1. Pre-Processing Steps 1.1 Data Reduction

The computing effort for the method described in detail below may be significantly reduced if the number of projections and the number of rows and columns in the object image space is coarsened in each direction by about one order of magnitude, i.e. about factor 10. A reduction factor by about 1,000 is then produced in three dimensions.

1.2 Smoothing Filtering

If estimates of path lengths in the object are derived from the projection values of the projection images, it is expedient to smooth the projections in advance in order to eliminate random variations due to noise, or local material inhomogeneities. A suitable smoothing algorithm is for example the filter algorithm developed in spectroscopy by Savitzky-Golay which is described in the publication SAVITZKY, A; GOLAY, M. J. E.: Smoothing and differentiation of data by simplified least squares procedures, Anal. Chem. 36 (1964), pages 1627-1639.

2. Method for the Case Where All Projection Images are Cropped

The following method is independent of the specific recording geometry and can be used for parallel beam and fan beam geometry equally.

We are assuming that the object is laterally extended in such a way that the detector 4 is not adequate for any direction of projection and therefore the boundaries of the object are cropped in all projections.

We are also supposing that the projection profile includes at least the projection value of the maximum object path length. This is plausible as it is nearly always only the less attenuated boundary regions of the object that are cropped.

Finally we are firstly simplistically assuming that the object consists of homogeneous material with a constant density. Section 5 describes one possible remedy in the case of inhomogeneous material distribution.

2.1 Sequence of the Processing Steps

First Step:

All projections are firstly processed one after the other. In the process the maximum value in the projection profile is determined for each projection k in a first method step and back projected along the associated projection beam into the projection image space. The associated path length W(k) in the object is then calculated from the maximum value in the projection profile. Details relating hereto are described in section 2.2.

Figure 3:
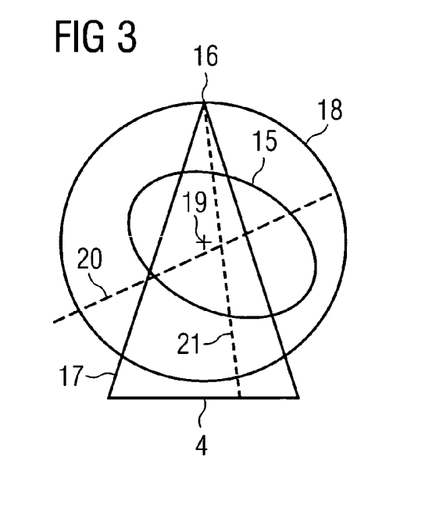
FIG. 3 shows a cross-section through the object being examined in FIG. 2, in which determination of an additional projection beam running through a central region of the object being examined is illustrated.
Figure 4:
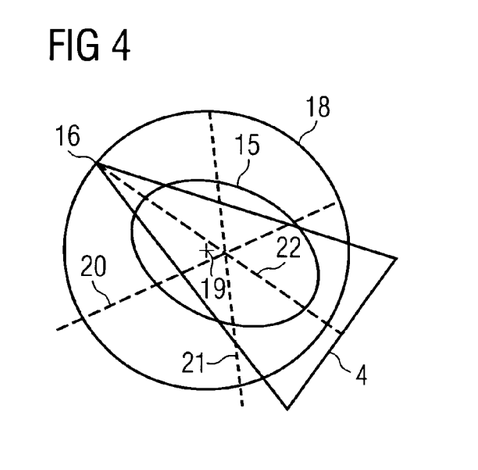
FIG. 4 shows a cross-section through the object being examined in FIGS. 2 and 3, in which determination of a third projection beam running through the central region of the object being examined is illustrated.

The first step is described in more detail with reference to FIGS. 2 to 4.

Figure 2:
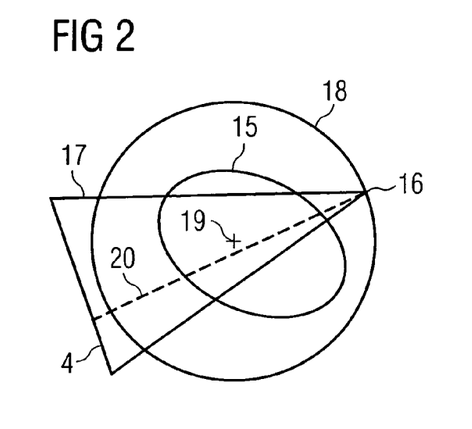
FIG. 2 shows a cross-section through an object being examined, with the aid of which determination of a projection beam running through the centre of the object being examined is illustrated.

FIG. 2 shows an object cross-section 15 which is X-rayed with X-ray radiation 17 by a tube focus 16 of the X-ray tube 3. The tube focus 16 revolves around the object cross-section 15 on a focus circle 18. The radiation 17 that passes through the object cross-section 15 is detected by the detector 4 that revolves around the object cross-section 15 on the opposing side thereof with the tube focus 16. In FIG. 2 the object cross-section 15 has an ellipsoidal shape and is eccentrically arranged with respect to a center of rotation 19 of the focus circle 18. The center of rotation 19 is the point of intersection of the axis of rotation 9, shown in FIG. 1, with the object image plane being considered, in which the object cross-section 15 is located.

Owing to the spatial extension and the eccentric position of the object cross-section 15 a truncated projection image is taken in the case of the angle of projection shown in FIG. 2. A projection value which is linked to a maximum attenuation of the X-ray radiation 17, can be sought inside the projection image that has been taken. A projection beam 20, which is the same as the back projection line of the pixel of the detector 4, can be associated with this projection value, which shows the projection value with maximum attenuation.

A truncated projection image is also taken in the case of the angle of projection shown in FIG. 3 by again determining a projection value linked with maximum attenuation and associating a projection beam 21 with this projection value. After determining the projection beams 20, 21 and 22 the associated object section W(k) in the object can be calculated from the projection value with maximum attenuation, which, as a rule, is equal to the maximum value in the projection image.

Figure 5:
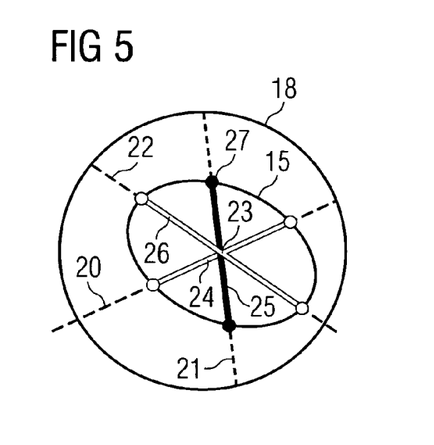
FIG. 5 shows a cross-section through the object being examined in FIGS. 2 to 4, in which determination of an object region is illustrated using end points of object sections plotted on the points of intersection of projection beams in FIGS. 2 to 4.

Second Step:

Once the last projection has been processed a point of intersection 23 of all back projection lines is determined, as shown in FIG. 5.

If there is no common point of intersection 23, and this is generally the case, a weighted center point S of the points of intersection $S_k$ can be formed:

$$\underline{S} = \frac{1}{\sum_{k=1,N} w_K} \sum_{k=1,N} w_K \underline{s_k} \quad (1)$$

It should be noted that in the case of n projection beams, among which there are no parallel ones, there are $N=(n^2-n)/2$ points of intersection.

The accuracy of point of intersection determination, which decreases with the angle of intersection, can be taken into account with the weights $W_k$. For example $w_k=|\sin(\beta_k)|$ can be selected, where $\beta_k$ is the acute angle between the projection beams.

It may be expedient to subsequently eliminate outliers by calculating the total according to equation (1) again but omitting all points which exceed a predefined maximum spacing a from S.

Third Step:

After determining the point of intersection 23 or the center point, the projections are processed again. In particular the path length W(k) is plotted on the associated back projection beam symmetrically to S for each projection k. If S does not lie on the respective back projection beam, and this is generally the case, S can firstly be projected onto the back projection line and then W(k) can be plotted symmetrically to this projected point.

In FIG. 5 object sections 24, 25 and 26 are associated by way of example with projection beams 20, 21 and 22 respectively and have each been symmetrically plotted on the point of intersection 23. Ideally the end points 27 of the object sections 24 to 26 are located at the boundary of the object cross-section 15.

Once all path lengths have been plotted, the boundary points form a polygon that surrounds the object region.

2.2 Determining the Path Length

The maximum logarithmic projection value in the projection being considered is p;

$$p=\log(I_0/I) \quad (2a)$$

where $$I=I_0 \exp(-\mu X) \quad (2b)$$

in which:

$I_0$ is the unattenuated measured intensity (without object)

I is the attenuated measured intensity (attenuation through path length X in object)

μ is the mean linear attenuation coefficient; the attenuation coefficient for soft tissue (for example water) or an estimated value formed according to the method outlined in section 5 for example can be used as the estimated value for μ.

From (2a), (2b) it follows for the path length that:

$$X=p/\mu \quad (3)$$

Equation (2b) is the Lambert-Beer law of attenuation for monochromatic radiation. The radiation of the X-ray tubes actually has a broad energy spectrum. The hardening effect associated therewith causes the mean attenuation coefficient to decrease with increasing material layer thickness. The polychromatic projection values are converted to the idealized case of a monochromatic reference energy using beam hardening correction methods. Such methods for the correction of radiation hardening are known for example from ZELLERHOFF, M.; SCHOLZ, B.; RÜH NSCHOPF, E.-P.; BRUNNER, T.: Low contrast 3D-reconstruction form C-arm data, Proceedings of SPIE, Medical Imaging 2005, vol. 5745, pages 646-655 and the technical literature disclosed therein. Equation (3) is again applicable following beam hardening correction.

As a rule the object cross-section taken consists of inhomogeneous material distribution with varying density and varying attenuation coefficients. How the path length can be approximately estimated in this case is outlined in section 5.

3. Method for the Event that not all Projection Images are Cropped

The method described in section 2, which will hereinafter be called the path length method for short, can also be applied to non-truncated projections but it is inexpedient to simply ignore the additional information that the complete projections contain instead of using it. This is particularly significant with regard to the combination method in section 3.2.

The following method in sections 3.1 and 3.2 can be applied to both parallel beam and fan beam/cone beam geometry.

3.1 Boundary Back Projection (Marginal Back Projection) Method

If none of the projections are cropped the object boundaries are also depicted in the projections. The convex envelope of the object region is obtained, as shown in FIG. 6, by back projection of just the object boundaries.

Figure 6:
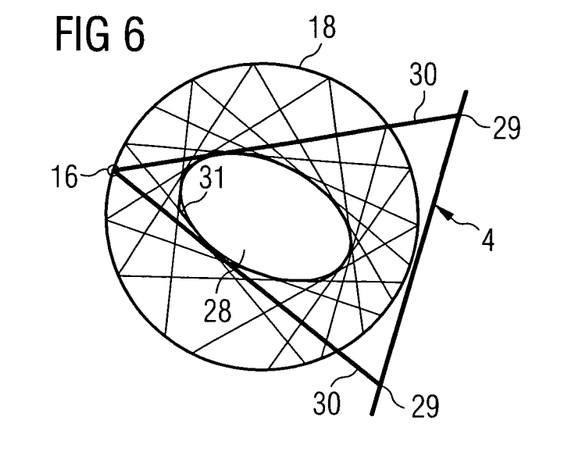
FIG. 6 shows a diagram of use of boundary beams of non-truncated projection images.

In the case shown in FIG. 6 an object cross-section 28 has such a small extension that the object cross-section 28 is fully depicted on all projection images. In this case object boundaries 29 can be determined in the projection image and by back projection boundary beams 30 can be determined which in their entirety enclose a convex hull polygon 31.

In this case the path length method from section 2 does not need to be used at all.

Figure 7:
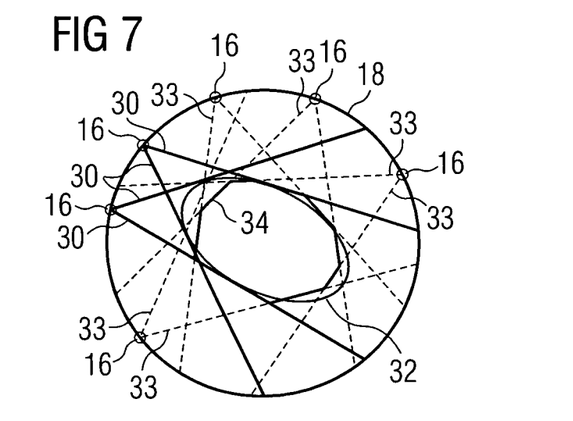
FIG. 7 shows a diagram of the boundary beams of truncated projection images.

If only some of the projections are cropped the object boundaries 29 are back-projected in the case of the complete projections but only the detector boundaries, instead of the object boundaries 29, are back projected in the case of the cropped projections. FIG. 7 shows a case of this kind. FIG. 7 shows an ellipsoidal object cross-section 32. The ellipsoidal object cross-section 32 is only completely depicted on the detector 4 in the case of angles of projection in which the object cross-section 32 is X-rayed along the longitudinal axis. The associated boundary beams 30 are indicated in FIG. 7 by solid lines. Detector boundary beams 33, by which boundaries of the detector 4 are back projected, are also reproduced in FIG. 7 by broken lines. The object boundary beams 30 and the detector boundary beams 33 surround a cropped hull polygon 34 which encloses the object cross-section 32 only in certain sections. Consequently the entire convex envelope of the object is no longer produced and instead is cropped according to FIG. 7.

To solve the problem section 3.2 describes a combination with the path length method from section 2.

3.2 Combination with the Path Length Method

First of all the boundary back projection method from section 3.1 is applied to the complete projections.

The path length method from section 2 should again be applied to the cropped projections.

Variations are possible in this case: the attenuation coefficient in equation (3) can for example be replaced by a corrected value according to section 5. It may also be advantageous if, instead of the center point of the points of intersection described in section 2, the object focal point is used, the determination of which is basically possible from complete projections. More detailed statements on determining the object focal point are described in section 3.3.

Figure 8:
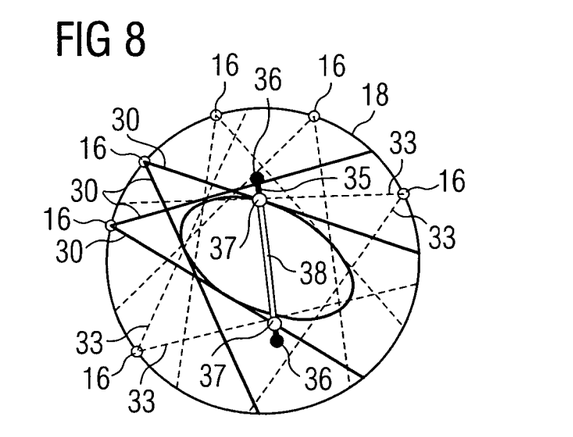
FIG. 8 shows a diagram of a correction of the method shown in FIGS. 2 to 5 with the aid of boundary beams of non-truncated projection images.

As the boundary back projection method is generally more accurate than the path length estimate according to section 2.2, at least in the case of inhomogeneous material, the results of the path length method in section 2 can be calibrated to a certain extent for the non-cropped projections because adjacent, complete projections provide tangents of the convex hull polygon 31 and, at a roughly perpendicular angle thereto, the extension of the object due to back projection of the object boundary beams 30. This geometric extension may generally be determined more accurately than the path length according to section 2.2, at least in the case of inhomogeneous attenuation coefficients, and allows a kind of calibration. FIG. 8 illustrates the substitution.

The path length can be corrected as follows in particular:

First Step:

Firstly the object boundary beams 30 of all complete projection images are created. This produces an image, corresponding to FIG. 7, without the detector boundary beams 33 shown in broken lines.

Second Step:

An object section 35 with end points 36 is then determined for each cropped projection image. The object section 35 has been determined according to the path length method of section 2 in this case.

Third Step:

In a further method step the innermost points of intersection 37 between the object boundary beams 33 and the object section 35 are determined. The innermost points of intersection 37 delimit a corrected object section 38.

With the corrected object section 38 the mean attenuation coefficient $\mu$ of the associated projection may be estimated more accurately than is disclosed in section 2.2 from projection value p and the geometric length X of the corrected object section by rearranging equation (3):

$$\mu = p/X \quad (3a)$$

3.3 Determining the Object Focal Point from Single Complete Projections

One component of the object focal point may be determined by way of the focal point of a complete parallel projection. This may easily be seen using the example of parallel projection in the direction of the y axis which is identical to the Radon transform with respect to the angle of projection at 90 degrees ($=\pi/2$) and which should be designated by:

$$R_\mu^{(\pi/2)}(x) = \int \mu(x,y) dy \quad (4a)$$

The total mass is:

$$m(\mu) = \iint \mu(x,y) dx dy = \int R_\mu^{(\pi/2)}(x) dx \quad (4b)$$

The focal point of the Radon transform with respect to the angle of projection at 90 degrees is then:

$$c(R_\mu^{(\pi/2)}) = \frac{\int x R_\mu^{(\pi/2)}(x) dx}{\int R_\mu^{(\pi/2)}(x) dx} \quad (4c)$$

$$= \frac{\int x \int \mu(x,y) dy dx}{m(\mu)}$$

$$= \frac{\iint x \mu(x,y) dx dy}{m(\mu)}$$

and this is exactly the x component of the focal point of the object density distribution $\mu(x,y)$.

This relationship applies accordingly to each position of the coordinate system. As the coordinate system can be rotated about the axis of rotation 9 as desired, two components of the object focal point, and therewith the (x, y) coordinates of the object focal point, can consequently be determined from two different directions of projection.

It should be noted that the above equations (4a-c) apply to parallel beam geometry. With fan beam geometry a conversion can be made to parallel beam geometry by what is known as rebinning. However this supposes that a sufficiently large number of complete directions of projection are available. Otherwise it is possible to manage as a result of the fact that the relationships (4a-c) also apply to fan beam geometry in a good approximation if the variables are interpreted as coordinates in fan beam geometry.

It should also be noted that for reasons of accuracy orthogonal directions of projection are optimal but, owing to the assumption that some of the projections are cropped, as a rule there are no orthogonal complete projections available. Directions of projection therefore have to be chosen in which the projection images are complete and which intersect at the greatest possible angles. Sometimes angles of intersection of less than 45 degrees have to be accepted in this respect. To take account of the inaccuracy as a function of the angles between the directions of projection it is therefore expedient to form a weighted mean value of the focal points analogously to the center point given in equation (1).

The object focal point determined in this manner can then replace the weighted center point formed according to equation (1) in section 2.1 and which has been formed from the points of intersection of the projection beams. The third step can then be repeated.

In addition it is possible to form a common weighted center point using the points of intersection determined according to section 2.1, and the focal points.

4. Extension to Three-Dimensional Cone Beam Geometry

The generalization of the method described in sections 2 and 3 to the three-dimensional case does not present any fundamental difficulties.

It is possible to limit a first approximation to application of the above-described method to the central object image plane in which the tube focus 16 is located. This tallies with the assumption that the object axially continues homogeneously from the central object plane, like a cylinder that is parallel to the axis of rotation 9, and this also roughly applies in many cases.

With slightly more effort the following procedure can be implemented:

Instead of an X-y plane the object image region comprises a stack of additional object image planes that are seated one above the other in the third dimension, designated z, and then form the object image volume. The detector 4 then comprises not one line but many lines arranged one above the other in the z dimension. A dramatic reduction in data, for example by a factor of 10, can advantageously be undertaken even in the case of object image planes seated one about the other in the z direction.

The X-rays run from the tube focus 16 to each detector pixel and form a radiation cone thereby. On its merits the radiation cone must be designated a radiation pyramid owing to the rectangular shape of the detector 4. The designation 'radiation cone' has become widely accepted, however. Back projection runs in the opposite direction—from the detector pixel through the object image volume to the tube focus 16.

The description in sections 2 and 3 may be transferred almost without modifications to each of the additional object image planes seated one above the other in the z direction.

Instead of the projection beams generally inclined toward the object image plane being considered, and the object beams, only the projections thereof into the respective object image plane have to be taken into account. The method steps described with reference to FIGS. 2 to 5 can then be taken.

In addition it is possible, even in the case of non-intersecting projection beams, to determine the respective connecting sections which are perpendicular to both projection beams. If a plurality of such connecting sections is determined a cloud 39 of connecting sections is produced from which a common center point can likewise be determined. By way of example, the section center point can be determined for each connecting section and a weighted or unweighted averaging, a common center point can be determined from the section center points.

5. Path Length Estimation in the Case of an Inhomogeneous Object

As a rule the object cross-section taken has inhomogeneous material distribution with varying density and varying attenuation coefficient. According to equation (3) in section 2.2 path length calculation therefore requires an at least approximate estimation of the attenuation coefficient μ. A suitable mean value can be estimated in the following steps:

The area inside the cropped polygon 34 shown in FIG. 7 is determined first of all:

$$F \tag{5a}$$

The center point of the cropped polygon 34 is then determined and its spacing $x_F$ from the X-ray focus calculated. The imaging enlargement ratio $V_F$ is also calculated:

$$V_F = \alpha_{FD}/x_F \tag{5b}$$

In this case $\alpha_{FD}$ is the spacing between focus and detector.

In a next method step the total $\Sigma(p)$ of the projection values in the cropped projection is determined.

Using the detector pixel spacing corrected by the enlargement ratio $V_F$:

$$\Delta y' = \Delta y / V_F \tag{5c}$$

a type of projection integral can then be formed:

$$J(p) = \Sigma(p)\Delta y' \tag{5d}$$

which is a good estimation of the integral of the attenuation coefficient over the area of the cropped polygon 34 as each individual projection value p is, as is generally known, a line integral of the attenuation coefficient.

It should be pointed out that the detector pixel spacing in equation (5c) is the pixel spacing that is greatly coarsened, i.e. increased, by data reduction.

The mean value of the attenuation coefficient over the cropped hull polygon then results as:

$$\mu' = J(p)/F \tag{6}$$

Inserting this estimated value in equation (3) produces an estimation of the path length.

However, before the third step in section 2.1 is executed therewith and a new boundary point entered, a smoothing can also be carried out. While the pre-processing by way of smoothing filtering mentioned in section 1.2 already contributes to the avoidance of outliers, because the construction of the hull polygon is based on estimates and on data afflicted by noise, it may be expedient to subsequently smooth the hull polygon by means of spine approximation for example.

A usability test can also be carried out. This usability test constitutes a precautionary measure against outliers. If, for example, the estimated path length is too long and the newly resulting end point 27 is located too far out, or if the end point 27 corresponds to an insufficient spacing of the object from the detector, and this contradicts constructional or geometric conditions given in advance, then this should be corrected accordingly.

6. Advantages of the Inventive Solution

If the actual extension of the object beyond the region cropped by the finite detector 4 is known, this knowledge is advantageous in several respects.

Knowledge of the object region contributes to the improvement in extrapolation algorithms, which are used to correct truncation artifacts, as previous knowledge of the required range of extrapolation can be used.

Knowledge of the object region is also advantageous for the post-reconstructive, iterative correction algorithm, for example if a correction of spectral beam hardening with inclusion of bones is carried out. A method of this kind is described for example in HSIEH, J.; MOLTHEN, R. C.; DAWSON, C. A.; JOHNSON, R. H.: An iterative approach to the beam hardening correction in cone beam CT, Med. Phys. 27(1), January 2000, pages 23-29.

Knowledge of the object region can also be used for correcting the scattered radiation if this is estimated from an already previously approximately reconstructed volume by means of deterministic or statistic models, for example with the aid of Monte Carlo simulations. A method of this type can be found for example in KYRIAKOU, Y,; RIEDEL, T.; KALENDER, W. A.: Combining deterministic and Monte Carlo calculations for fast estimation of scatter intensities in CT, Phys. Med. Biol. 51 (2006), pages 4567-4586.

Localizing the object region, i.e. the volume region, in which the object is located and to which reconstruction can meaningfully be limited, allows a reduction in the number of voxels to be reconstructed and therefore the computing effort required for back projection which makes up the major part of the computing time of the reconstruction algorithms for reconstructing the object images.

With iterative algebraic reconstruction methods (of the ART type) a wide variety of previous information can be easily incorporated and lead to stabilization, acceleration and improvement in accuracy. It is plausible for consideration of previous knowledge of the carrier quantity of the object to be advantageous: not only is computing time reduced, but faster convergence may also be expected if in the correction step of back projection the correction is distributed only among the relevant pixel range and not among an unnecessary, large pixel range. A reconstruction method of this kind is described in BENSON, T. M.; GREGOR, J.: Framework for Iterative Cone-Beam Micro-CT Re-construction, IEEE Trans. Nucl. Science, vol. 52, no. 5, October 2005, pages 1335-1340, Non-truncated projection images are assumed in this method, however.

Finally it should also be emphasized that the computing effort for determining the object region can be kept within limits if the data is reduced by one order of magnitude respectively in each dimension before carrying out determination of the object region.

Finally it should also be pointed out that features and properties which have been described in connection with a specific exemplary embodiment may also be combined with a further exemplary embodiment, apart from when this is ruled out for compatibility reasons.

Finally is should also be pointed out that in the claims and description the singular includes the plural, apart from when something different emerges from the context. Both the singular and the plural are meant in particular when the indefinite article is used.

The invention claimed is:

1. A computer tomography method for determining a region taken up by an object being examined with the aid of projection images, comprising:
   generating radiation via a radiation source;
   loading a detector with the radiation and taking via the detector projection images of the object from various directions of projection;
   creating object images via an evaluation unit connected downstream of the detector;
   determining a position of a central region using at least two of the projection images via the evaluation unit;
   determining object sections from projection image values of the projection images via the evaluation unit;
   plotting the object sections on the central region via the evaluation unit; and
   determining an object region using end points of the plotted object sections via the evaluation unit,
   wherein for determining an object section a mean attenuation coefficient of the object being examined is estimated by totaling projection image values associated with an object image plane, and the total is divided by an area of an at least approximately determined object region.

2. The method as claimed in claim 1, wherein the position of the central region is determined in truncated projection images.

3. The method as claimed in claim 1, wherein the object sections are symmetrically plotted on the central region.

4. The method as claimed in claim 1, wherein projection beams with respective maximum attenuations through the object are respectively sought in at least two of the projection images for determining the central region, and proximity regions of the projection beams are then determined.

5. The method as claimed in claim 4, wherein a number of points of intersection is determined from pairs of the projection beams.

6. The method as claimed in claim 5, wherein a common central point used as the central region is fixed inside a cloud formed by the points of intersection.

7. The method as claimed in claim 6, wherein the common central point is determined by a weighted averaging of the points of intersection, and the weight allocated to a point of intersection decreases with acute angle between the projection beams.

8. The method as claimed in claim 6, wherein the object sections are plotted on the common central point projected on a respective projection beam.

9. The method as claimed in claim 1, wherein a common central point used as the central region is determined in that a focal point of the object being examined is determined using non-truncated projection images.

10. The method as claimed in claim 1, wherein object boundary beams are determined in non-truncated projection images and a corrected object section, which is limited by innermost points of intersection of the object boundary beams, is determined with respect to the object section plotted on the central region.

11. The method as claimed in claim 10, wherein an attenuation coefficient is determined for an associated projection beam with the corrected object section.

12. The method as claimed in claim 1, wherein the object section is determined by assuming an attenuation coefficient typical for the object being examined.

13. The method as claimed in claim 1, wherein a hull polygon of the object region is determined using the end points of the object sections.

14. The method as claimed in claim 1, wherein the object region is determined in an object image plane encompassing a radiation focal point of the radiation source.

15. The method as claimed in claim 1, wherein the object region is determined in an object image plane that does not encompass a radiation focal point of the radiation source by using projection of projection beams and the object sections into the object image plane.

16. The method as claimed in claim 1, wherein the projection images are smoothed before determining the object region.

17. The method as claimed in claim 1, wherein a resolution of data used for determining the object region is coarsened before determining the object region.

18. The method as claimed in claim 1, wherein X-ray radiation is used for examining the object.

19. A device for computer tomography, comprising:
   a radiation source for generating radiation;
   a detector for taking projection images of an object being examined from different directions of projection; and
   an evaluation unit connected downstream of the detector for generating object images of the object using the projection images, where the evaluation unit is configured to:
      create object images;
      determine a position of a central region using at least two of the projection images;
      determine object sections from projection image values of the projection images;
      plotting the object sections on the central region; and
      determine an object region using end points of the plotted object sections,
   wherein for determining an object section a mean attenuation coefficient of the object being examined is estimated by totaling projection image values associated with an object image plane, and the total is divided by an area of an at least approximately determined object region.

* * * * *